United States Patent
Brueck et al.

(10) Patent No.: US 8,663,661 B2
(45) Date of Patent: Mar. 4, 2014

(54) SOLID PHARMACEUTICAL DOSAGE FORM OF TICAGRELOR

(75) Inventors: Sandra Brueck, Munich (DE); Dominique Meergans, Munich (DE)

(73) Assignee: ratiopharm GmbH, Ulm (DE)

( * ) Notice: Subject to any disclaimer, the term of this patent is extended or adjusted under 35 U.S.C. 154(b) by 0 days.

(21) Appl. No.: 13/518,450

(22) PCT Filed: Dec. 20, 2010

(86) PCT No.: PCT/JP2010/070268
§ 371 (c)(1),
(2), (4) Date: Jul. 9, 2012

(87) PCT Pub. No.: WO2011/076749
PCT Pub. Date: Jun. 30, 2011

(65) Prior Publication Data
US 2013/0028938 A1    Jan. 31, 2013

(30) Foreign Application Priority Data
Dec. 23, 2009 (EP) .................................. 09180628

(51) Int. Cl.
*A61K 9/00* (2006.01)
(52) U.S. Cl.
USPC ..................................................... 424/400
(58) Field of Classification Search
None
See application file for complete search history.

(56) References Cited

U.S. PATENT DOCUMENTS

| | | | | |
|---|---|---|---|---|
| 6,634,576 B2 * | 10/2003 | Verhoff et al. | ................... | 241/21 |
| 2007/0003615 A1 * | 1/2007 | Jenkins et al. | ................ | 424/464 |
| 2008/0254036 A1 * | 10/2008 | Sinha et al. | ................. | 424/141.1 |
| 2009/0048216 A1 * | 2/2009 | Gretler et al. | .................. | 514/159 |
| 2010/0183598 A1 * | 7/2010 | Schultz et al. | ............. | 424/133.1 |

FOREIGN PATENT DOCUMENTS

| | | | |
|---|---|---|---|
| CN | 102657629 A | * | 9/2012 |
| WO | WO 01/92262 | | 12/2001 |
| WO | WO 0192262 A1 | * | 12/2001 |
| WO | WO 2007146712 A2 | * | 12/2007 |
| WO | WO 2008/024044 | | 2/2008 |
| WO | WO 2008/024045 | | 2/2008 |
| WO | WO 2008024044 A1 | * | 2/2008 |
| WO | WO 2008024045 A1 | * | 2/2008 |
| WO | WO 2009007675 A2 | * | 1/2009 |
| WO | WO 2009087410 A2 | * | 7/2009 |

OTHER PUBLICATIONS

Buckton, G. et al., International Journal of Pharmaceuticals, vol. 82, No. 3, pp. R7-R10 (May 25, 1992).
Jolanta M. Siller-Matula et al., "Pharmacokinetic, pharmacodynamic and clinical profile of novel antiplatelet drugs targeting vascular diseases", *British Journal of Pharmacology* (2010), vol. 159, pp. 502-517.
Reinhard Vehring, "Pharmaceutical Particle Engineering via Spray Drying", *Pharmaceutical Research* (May 2008), vol. 25, No. 5, pp. 999-1022.
Rong Liu, *Water-Insoluble Drug Formulations*, CRC Press (2008), p. 84 ("Particle Size").

* cited by examiner

*Primary Examiner* — Robert A Wax
*Assistant Examiner* — Olga V Tcherkasskaya
(74) *Attorney, Agent, or Firm* — Chalin A. Smith; Smith Patent Consulting

(57) ABSTRACT

The present invention relates to a solid pharmaceutical dosage form comprising ticagrelor as pharmaceutically active ingredient, to certain particles of ticagrelor and to processes of preparing the same.

19 Claims, No Drawings

SOLID PHARMACEUTICAL DOSAGE FORM OF TICAGRELOR

This application corresponds to the national phase of International Application No. PCT/EP2010/070268 filed Dec. 20, 2010, which, in turn, claims priority to European Patent Application No. 09.180628.1 filed Dec. 23, 2009, the contents of which are incorporated by reference herein in their entirety.

The present invention relates to a solid pharmaceutical dosage form comprising ticagrelor as pharmaceutically active ingredient, to certain particles of ticagrelor and to a process of preparing the same.

The compound, [1S-[1α,2α,3β(1S*,2R*),5β]]-3-[7-[[2-(3,4-difluorophenyl)cyclopropyl]-amino]-5-(propylthio)-3H-1,2,3-triazolo[4,5-d]pyrimidin-3-yl]-5-(2-hydroxyethoxy)-cyclopentane-1,2-diol is known as ticagrelor and is represented by the formula (I) below:

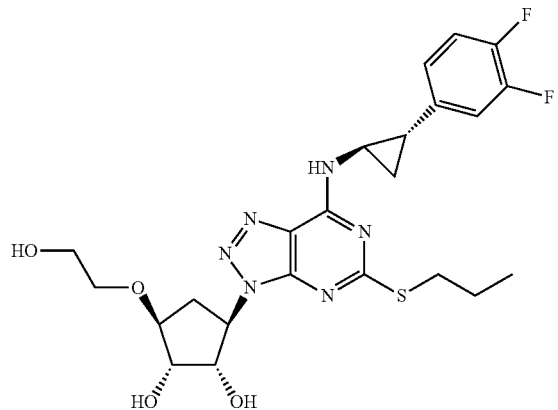

Formula (I)

Ticagrelor can be prepared according to the methods disclosed in WO 99/05143. This document also discloses that ticagrelor exhibits activity as $P2Y_{ADP}$ receptor antagonist.

ADP induced platelet aggregation is mediated by the $P2Y_{ADP}$ receptor subtype located on the platelet membrane. The $P2Y_{ADP}$, an G-protein coupled receptor is primarily involved in mediating platelet aggregation/activation. The pharmacological characteristics of this receptor have been described by Humphries et al. in Br. J. Pharmacology (1994), 113, 1057-1063 and by Fagura et al. in Br. J. Pharmacology (1998), 124, 157-164.

Platelet adhesion and aggregation are initiating events in arterial thrombosis. Although the process of platelet adhesion to the sub-endothelial surface have an important role to play in the repair of damaged vessel walls, misdirected platelet aggregation can initiate acute thrombotic occlusion of vital vascular beds leading to events with high morbidity such as myocardial infarction and stable angina.

Furthermore ticagrelor is indicated for use in the treatment of CNS disorders and prevention of the growth and spread of tumors.

According to WO 01/92262 ticagrelor exists in four different crystalline forms and an amorphous form. In the pharmaceutical dosage forms of the present invention any of these forms can be used.

Pharmaceutical compositions comprising ticagrelor are disclosed in WO 2008/024044 and WO 2008/024045. It is disclosed that the compositions which may contain up to 50% by weight of the active ingredient are suitable for oral administration and that they release substantially all of the active ingredient. The preparations are prepared according to a conventional manner using a wet granulation process.

For ticagrelor there still exists the problem that this pharmaceutically active compound exhibits only low solubility. The poor solubility of drug is a significant problem in the design of pharmaceutical formulations. Ticagrelor is hardly soluble in a neutral medium such as water. Consequently, water is the most suitable test medium for evaluating non-bioequivalence on conducting a dissolution test. In developing a solid oral dosage forms comprising ticagrelor as an active ingredient, it is desirable to find a formulation having a good dissolution property in water. Solid oral dosage forms comprising ticagrelor as an active ingredient are desired to show good dissolution properties in the first fluid, which is corresponding to gastric juice, in a dissolution test.

Therefore, it would be desirable to provide a pharmaceutical preparation which not only releases substantially all of the active ingredient but additionally provides a fast dissolution of the active ingredient. Moreover, in particular with respect to patient compliance, it would be desirable to provide a pharmaceutical composition having a high drug load but nevertheless being easily to be prepared and stable while maintaining the beneficial properties with respect to fast solubility and bioavailability. These and other problems are solved by the present invention.

It has now been found that the above problems can be solved if the particles of the pharmaceutically active ingredient, ticagrelor, have a certain particle size. It was found that if at least 90% by volume of the ticagrelor particles have a particle size in the range of 1 µm to 150 µm, a solid pharmaceutical dosage form comprising these particles exhibits beneficial effects in particular with regard to improved dissolution rate. As a result thereof, the dosage form of the present invention provides a rapid achievement of maximum blood concentration of the $P2Y_{ADP}$ inhibitor and/or a rapid onset of the therapeutic $P2Y_{ADP}$ inhibitory effect.

Thus, the present invention relates to a solid pharmaceutical dosage form comprising ticagrelor or a pharmaceutically acceptable salt or ester thereof, characterized in that at least 90% by volume of the ticagrelor particles have a particle size in the range of 1 µm to 150 µm.

The ticagrelor particles can be amorphous or in any other polymorphic crystalline form. The polymorphic forms include hydrates, solvates, co-crystals, etc. Moreover, the ticagrelor can be present in its free base form or in the form of any pharmaceutically acceptable salt or ester known to a person skilled in the art. As salts those of inorganic or organic acids can be exemplified, such as hydrochloride, sulfate, mesylate, tosylate, besylate, etc. As esters those of organic acids can be exemplified, such as acetate.

It is understood that any reference to "ticagrelor particles" covers particles of ticagrelor free base as well as pharmaceutically acceptable salts or esters of ticagrelor.

Preferably, at least 95% by volume, more preferable at least 98% by volume of the ticagrelor particles in the solid pharmaceutical dosage form of the present invention have a particle size in the range of 1 µm to 150 µm, preferably in the range of 3 µm to 130 µm, more preferable in the range of 5 µm to 120 µm, such as in the range of 10 µm to 100 µm, whereby any combinations of the lower and upper limits of these ranges are also intended to be covered by the present invention.

In a further embodiment of the present invention the ticagrelor particles have a mean particle size $D_{50}$ in the range of 30 μm to 70 μm, preferably in the range of 40 μm to 60 μm, more preferably of about 50 μm.

The term "particle size" of a certain particle according to the invention refers to the diameter of an equivalent product being assumed to be spherical and showing the same light scattering pattern as the particle. According to the invention the particle size is measured via laser light diffraction technique. The laser light diffraction technique used for the determination of particle size and its distribution is based on the analysis of the diffraction pattern produced when particles are exposed to a beam of monochromatic light. The laser light diffraction uses the scattering of light caused by interaction of the laser light with the particles to determine the particle size.

The term "particle size distribution" as used herein assume refers to the statistical distribution of the volume share related of all particle sizes.

Herein the particle size distribution of the particle size $D_{50}$ value is defined such that 50% by volume of the particles have a particle size smaller than the $D_{50}$ value and 50% by volume of the particles have a greater particle size greater than the $D_{50}$-value.

For determining the particle size a Mastersizer 2000 from Malvern Instruments is used. A wet measurement on a dispersion of the particles in a dispersing agent at 25° C., 2000 rpm, 30 sec ultrasound is preferred.

The analysis is carried out with assistance of the Mie method for particle $D_{50}$ smaller than 5.0 μm and the Fraunhofer method for particle $D_{50}$ greater than 5.0 μm. The Fraunhofer diffraction theory is generally used for particle fractions which are significantly larger than the wavelength of the laser light ("Pharmaceutics The science of dosage form design", 1998). Furthermore the Mie theory defines the secondary scattering caused by refraction of light within small particles as stated in the international norms of laser diffraction measurement (ISO13320-1 (1999)).

The particle size distribution according to the invention can be monomodal or bimodal. In the preferred embodiment of the invention the particle size distribution of the active agent is monomodal. The term "monomodal" as used herein refers to only one peak observed in the histogram and/or a graph of the frequency distribution.

Furthermore, it has surprisingly been found that contrary to the teaching of WO 2008/024045 it is possible to provide solid pharmaceutical dosage forms having a high drug load and nevertheless exhibiting an improved dissolution rate. Therefore, the present invention also relates to a solid pharmaceutical dosage form comprising more than 50% by weight of ticagrelor or a pharmaceutically acceptable salt or ester thereof, based on the total weight of the dosage form.

The improved fast dissolution rate of the pharmaceutical dosage form comprising more than 50% by weight of ticagrelor can for example be achieved by using either ticagrelor particles having the above defined certain particle size and/or by the addition of at least one hydrophilic polymer and/or emulsifier.

Preferably, the solid pharmaceutical dosage form which comprises more than 50% by weight of ticagrelor or a pharmaceutically acceptable salt or ester thereof, based on the total weight of the dosage form, contains the active ingredient in a form such that at least 90% of the ticagrelor particles have a particle size in the range of 1 μm to 150 μm (wherein the preferred ranges are defined as above) and the dosage form additionally comprises at least one hydrophilic polymer and/or emulsifier.

In one embodiment of the present invention the weight ratio of ticagrelor or a pharmaceutically acceptable salt or ester thereof to the hydrophilic polymer and/or emulsifier in the solid pharmaceutical dosage form is in the range of 100:1 to 1:1, preferably 100:1 to 2:1.

The hydrophilic polymer can be selected from known polymers having polar groups. Examples of polar groups are hydroxy, amino, carboxy, carbonyl, ether, ester and sulfate. Polymers containing hydroxy groups are preferred.

Examples of suitable hydrophilic polymers are cellulose derivatives, such as hydroxypropylmethyl cellulose (HPMC), hydroxypropyl cellulose (HPC), carboxymethyl cellulose (CMC), preferably as sodium or calcium salt, hydroxyethyl cellulose (HEC), polyvinylpyrrolidone (PVP), preferable having a molecular weight in the range of 10,000 g/mol to 60,000 g/mol, copolymers of polyvinylpyrrolidone, preferably copolymers comprising vinylpyrrolidone and vinylacetate units (e.g Povidon, VA64, BASF), preferably having a molecular weight in the range of 40,000 g/mol to 70,000 g/mol, polyoxyethylenalkyl ether, polyethylenglycol, co-block-polymers of ethylenoxide and propyleneoxide (poloxamer, pluronic), polymethacrylate derivatives, polyvinyl alcohol, polyvinyl alcohol derivatives and polyethylenglycol derivatives. Preferred hydrophilic polymers are polyvinylpyrrolidone, copolymers of polyvinylpyrrolidone and hydroxypropylmethyl cellulose.

Emulsifiers which can be used in the solid pharmaceutical dosage form of the present invention are carboxylic acids and salts and ester thereof, sulfonic acids and salts thereof, alkyl-sulfate-alkylethersulfonic acids, phosphoric acid esters and salts thereof, acylamino acids and salts thereof, alkylamine salts, quaternary ammonium compounds and esters thereof, ethoxylated alkylamines and non-ionic tensides, e.g. fatty alcohols, ethylenoxids, alkanolamides, alkoxylated polysiloxanes, glycerol esters, etc.

The pharmaceutical dosage form according to the present invention can further comprise additional excipients and adjuvants, which are pharmaceutically acceptable, and general coating materials, which are preferably applied as a coating to the pharmaceutical dosage form of the present invention. Such further excipients and adjuvants are known to the person skilled in the art. In this regard it can be referred to the standard textbook by Fiedler ("Lexikon der Hilfsstoffe für Pharmazie, Kosmetik und angrenzende Gebiete", 5$^{th}$ ed., 2002) and to the "Handbook of Exipients", edited by the American Pharmaceutical Association and Dr. Arthur H. Kibbe, 3$^{rd}$ ed., 2000.

In particular the pharmaceutical dosage form according to the present invention comprises one or more diluents, binders, lubricants and/or coating materials and optionally colourants and/or surfactants, and in particular 0 to 40% by weight of a diluent, 0 to 30% by weight of a binder, 0 to 6% by weight of a disintegrant, 0 to 2% by weight of a lubricant, 0 to 3% by weight of a glidant, 0 to 3% by weight of a coating material, and optionally 0 to 6% by weight of a surfactant and 0 to 3% by weight of a colourant, each based on the total weight of the composition. The excipients and adjuvants and optionally coating materials or colourants are present in the pharmaceutical composition of the present invention, such that the total amount of the pharmaceutical composition results in 100% by weight. If not stated otherwise all % by weight figures herein are based on the total weight of the dosage form, including any shell or coating, if present.

As diluent one or more components can be used, which contribute part of the dosage form to reach the necessary total mass of the dosage form. Preferable diluents are inorganic phosphates, like dibasic calcium phosphate, or sugars or sugar analogues and derivatives thereof, in particular lactose, such as lactose monohydrate or water-free lactose, dextrose, sorbit, mannit, saccharose, maltodextrin, isomalt and tablettose. Mannitol or cellulose like microcrystalline cellulose or powdered celluloses are also preferable diluents according to the present invention. Preferably the pharmaceutical dosage form according to the present invention comprises 5 to 40% by weight, more preferable 10 to 40% by weight, even more preferable 20-40% by weight, of a diluent.

Binders are compounds able to bind together active ingredient and excipients in a mixture. As binder to be used in the pharmaceutical dosage form of the present invention polyvinylpyrrolidon (PVP) preferably having the molecular weight of 10,000 to 60,000 g/mol and copolymers of PVP preferably having a molecular weight of 40,000 to 70,000 g/mol and hydroxypropylmethyl cellulose are especially preferred. The binder is usually present in an amount of 0 to 30% by weight, preferably 2 to 27% by weight, in particular 5 to 25% by weight, based on the total weight of the dosage form.

As disintegrant one or more components can be used, which decompose the tablet in the gastrointestinal fluid. Preferable disintegrants are alginates, pregelatinized starch, modified starch like croscarmellose and crosslinked PVP like collidone and crospovidon. Crospovidone and croscarmellose are preferable disintegrants according to the present invention. Preferably the pharmaceutical dosage form according to the present invention comprises 1 to 10% by weight, more preferable 2 to 8% by weight, even more preferable 3 to 5% by weight, such as about 4% by weight of a disintegrant based on the total weight of the pharmaceutical dosage form.

Additional excipients to be used in the pharmaceutical dosage form of the present invention are glidants, such as silicium dioxide, which are added to a powder to improve its flowability; and/or amphipatic wetting agents, such as sodium lauryl sulfate (SDS), glycerol monostearate, triglycerides or glycerol behenate.

Optionally, as lubricants can be used in the pharmaceutical dosage forms of the present invention fatty acids or fatty acid derivates, such as alkali and earth alkali salts of stearic, lauric and/or palmitic acid. Sodium stearyl fumarate and magnesium stearate are preferred. The lubricant is optionally present in an amount of 0 to 3% by weight, preferably 0.5 to 2.5% by weight, such as about 2% by weight, based on the total amount of the dosage form.

An advantage of the pharmaceutical dosage form of the present invention is that a lubricant is not necessarily required in its preparation. Therefore, in one embodiment the dosage form does not comprise any lubricant.

The solid pharmaceutical dosage form of the present invention preferably is an oral pharmaceutical dosage form, such as a tablet, capsule, granules, pellets or sachets. The pharmaceutical dosage form can be prepared by methods known in the art, such as tabletting by melt granulation or direct compression.

The compression of the blend to tablet cores can be carried out using a conventional tabletting machine or a rotary compression machine. The tablet cores may vary in shape and can be, for example, round, oval, oblong, cylindrical or any other suitable shape. The cores may also vary in size depending on the concentration of the therapeutic agent.

The pharmaceutical dosage form according to the present invention comprising ticagrelor may be present in form of a tablet which is coated with one or more coating materials. The coating materials are not particularly limited and are known to the person skilled in the art. As far as it is herein referred to a dissolution profile, the dissolution profile is that of an uncoated tablet, if the tablet is not coated, and that of a coated tablet, if the tablet is coated.

In the pharmaceutical dosage form of the present invention the active ingredient, ticagrelor, is usually formulated in dose units. The dose unit contains from 50 to 300 mg, advantageously from 70 to 240 mg, preferably from 90 to 180 mg of ticagrelor calculated as ticagrelor free base. Such a dosage form is normally administered from 2 to 4 times daily, preferably 2 times daily. The preferred unit dosage forms include tablets and capsules.

Another object of the present invention is to provide a solid oral dosage form containing ticagrelor in combination with an anti-thrombotic agent and a process of forming the same. The anti-thrombotic compound is selected from anti-platelet agents, anticoagulant agents and fibrinolytic agents. Anti-thrombotic agent selected from antiplatelet agents include ASA (acetylsalicylic acid), clopidogrel, ticlopidine, dipyridamole, GPIIb/IIIa antagonists; anti-coagulants such as thrombin inhibitors, warfarin, factor Xa inhibitors, heparin; and fibrinolytic agents including but not limited to, streptokinase and tenecteplase.

Particularly the subject of the present invention includes a solid oral dosage form containing ticagrelor in a combination with ASA.

Acetylsalicylic acid is often used as an analgesic, anti-pyretic and anti-inflammatory medication but also known as antiplatelet agent inhibiting the production of thromboxane and therefore as a result prevent heart attacks, strokes and blood clot formation. ASA have an inhibition of the enzyme cyclooxygenase that is responsible for important biological mediators including thromboxane.

The present invention particularly relates to a solid oral dosage form, which contains a unit dose in the range of about 10 to 250 mg, preferably in the range of about 50 to 200 mg, particularly of 90 or 180 mg of the active ingredient ticagrelor and a unit dose in the range of about 6 to 60 mg, preferably in the range of about 30 to 500 mg, particularly of 50 or 100 mg of the active ingredient acetylsalicylic acid.

Respective formulations comprising ticagrelor and/or other antithrombotic agent may be administered, sequentially, separately and/or simultaneously, over the course of treating the relevant condition, which condition may be acute or chronic.

The present invention furthermore provides a process for the preparation of the above solid pharmaceutical dosage form which comprises the step of milling ticagrelor or a pharmaceutically acceptable salt or ester thereof in the presence of a polymer and/or emulsifier. In this process, the polymer can be hydrophilic or amphiphilic. Hydrophilic polymers are preferred. Most preferred are those hydrophilic polymers which are exemplified above. Suitable amphiphilic polymers are for example gylcerol monostearat, triglyceride and glycerol behenate. Suitable emulsifiers are those as exemplified above.

The milling can be carried out as wet milling or dry milling. If necessary the milled particles after wet milling can be dried by drying methods known in the art, such as spray drying, vacuum drying and lyophilization.

The milled ticagrelor particles or mixture of particles can then be processed into solid pharmaceutical dosage forms by methods known in the art, such as direct compression, dry or wet granulation followed by compression or melt extrusion also followed by compression. Other known processing steps, such as spray coating, may also be employed.

The invention will now be further explained by way of examples which are not construed to be limiting.

EXAMPLE 1

| Ingredients | Function | mg/Tab | % w/w |
|---|---|---|---|
| Ticagrelor | Active | 90.0 | 50.0 |
| Mannitol | Diluent | 72.0 | 40.0 |
| Povidon | Binder | 9.0 | 5.0 |
| Crospovidon | Disintegrant | 7.2 | 4.0 |
| Magnesium stearate | Lubricant | 1.8 | 1.0 |
| | Total Weight | 180.0 | 100.0 |

Ticagrelor particles were prepared using a dry grinding process. A mixture of ticagrelor and part of the mannitol was ground in a ball mill. Subsequently the remaining excipients with the exception of magnesium stearate were added to the blend and mixed in a freefall mixer. The lubricant, magnesium stearate, was sifted and mixed with the blend. The final blend was then compressed into tablets using a suitable tablet press and then optionally coated with a coating material, e.g. Opadry.

EXAMPLE 2

| Ingredients | Function | mg/Tab | % w/w |
|---|---|---|---|
| Ticagrelor | Active | 90.0 | 52.0 |
| Lactose | Diluent | 72.0 | 41.6 |
| Maize starch | Disintegrant | 11.0 | 6.4 |
| | Total Weight | 173.0 | 100.0 |

The tablets were prepared using a process similar to the process described in example 1.

EXAMPLE 3

| Ingredients | Function | mg/Tab | % w/w |
|---|---|---|---|
| Ticagrelor | Active | 90.0 | 54.9 |
| Isomalt | Diluent | 72.0 | 43.9 |
| Magnesium stearate | Lubricant | 2.0 | 1.2 |
| | Total Weight | 164.0 | 100.0 |

Ticagrelor particles were prepared using a dry grinding process. Ticagrelor was crushed using an air jet mill. Subsequently the diluent were added to the active agent and mixed in a freefall mixer. The lubricant, magnesium stearate was sifted and mixed with the blend. The final blend was then compressed into tablets using a suitable tablet press and then optionally coated with a coating material, e.g. Opadry.

EXAMPLE 4

| Ingredients | Function | mg/Tab | % w/w |
|---|---|---|---|
| Ticagrelor | Active | 90.0 | 48.3 |
| Hydroxy propyl methyl cellulose (HPMC) | Binder | 18.0 | 9.7 |
| SDS | Wetting agent | 4.5 | 2.4 |
| Mannitol | Diluent | 64 | 34.3 |
| Croscarmellose | Disintegrant | 7.2 | 3.9 |
| Silica | Glidant | 0.9 | 0.5 |
| Magnesium stearate | Lubricant | 1.8 | 1.0 |
| | Total Weight | 186.4 | 100.0 |

Ticagrelor particles were prepared using a wet grinding process. The co-grinding was performed with ticagrelor together with HPMC and SDS within a dispersing agent using a wet mill. Subsequently the suspension was spray dried. Half of mannitol, croscarmellose and silicium dioxide were added to the dried intermediates, were blended and compacted. The compacted particles were sifted, afterwards the remaining excipients were added and blended. The final blend was then compressed into tablets using a suitable tablet press and then optionally coated with the coating material, e.g. Opadry.

EXAMPLE 5

| Ingredients | Function | mg/Tab | % w/w |
|---|---|---|---|
| Ticagrelor | Active | 90.0 | 46.7 |
| Povidone | Binder | 45.0 | 23.4 |
| SDS | Wetting agent | 1.0 | 0.5 |
| Microcrystalline cellulose | Diluent | 45.0 | 23.4 |
| Croscarmellose | Disintegrant | 9.0 | 4.7 |
| Silica | Glidant | 0.9 | 0.5 |
| Magnesium stearate | Lubricant | 1.8 | 0.9 |
| | Total Weight | 192.7 | 100.0 |

Ticagrelor, povidone, SDS and half of croscarmellose and crystalline cellulose were mixed and heated forming melt granules using a heated high shear mixer. The melt granules were sifted and mixed with the remaining excipients in exception of the lubricant in a freefall mixer. Subsequently the lubricant magnesium stearate was added.

EXAMPLE 6

| Ingredients | mg/Tab |
|---|---|
| Ticagrelor | 90 |
| ASA | 37.5-100 |
| Mannitol | 72 |
| Povidon 25 | 9.0 |
| Crospovidon | 7.2 |
| Magnesium stearate | 1.8 |

Ticagrelor particles were prepared using a dry grinding process. The co-grinding was performed with ticagrelor together with mannitol using a ball mill for 1 hour. ASA was grinded separately and afterwards added to the mixture of grinded ticagrelor and mannitol. Subsequently, the remaining ingredients, except magnesium stearate, were added and mixed for 10 minutes in a free fall mixer. Magnesium stearate was added through a 0.5 mm sieve and the resulting mixture was mixed for further 3 minutes. The resulting material was directly compressed on a Korsch eccentric press.

EXAMPLE 7

| Ingredients | mg/Tab |
|---|---|
| Ticagrelor | 90 |
| ASA | 37.5-100 |
| HPMC | 18 |
| SDS | 4.5 |
| Mannitol | 32 + 32 |
| Croscarmellose | 7.2 |
| Silica | 0.9 |
| Magnesium stearate | 1.8 |

Ticagrelor was milled together with HPMC and SDS in a dispersion medium for 1 hour in a Netsch microCer. The obtained suspension was spray dried in a Büchi spray tower. The resulting mixture was mixed for 10 minutes in a free fall mixer (Turbula TB10) together with the previously grinded ASA, half amount of the mannitol, croscarmellose and silica. The mixture was then compacted. The product was sieved using a coMill sieve (1000 μm), followed by adding the remaining excipients and the magnesium stearate being previously sieved through a 0.5 mm sieve. The resulting mixture is mixed for further 3 minutes. The final mixture was pressed into tablets using a Korsch eccentric press EK0.

The invention claimed is:

1. A solid pharmaceutical dosage form comprising particles of ticagrelor or a pharmaceutically acceptable salt or ester thereof, characterized in that at least 90% by volume of the ticagrelor particles have a particle size in the range of 1 μm to 150 μm.

2. The solid pharmaceutical dosage form according to claim 1, further comprising at least one hydrophilic polymer and/or emulsifier.

3. The solid pharmaceutical dosage form according to claim 2, wherein the weight ratio of ticagrelor or salt or ester thereof to the hydrophilic polymer and/or emulsifier ranges from 100:1 to 1:1.

4. The solid pharmaceutical dosage form according to claim 2, wherein the hydrophilic polymer is selected from the group consisting of cellulose derivatives, polyvinylpyrrolidone, copolymers of polyvinylpyrrolidone, polyoxyethylenealkyl ether, polyethylenglycol, co-block-polymers of ethylenoxide and propylenoxide, polymethacrylate derivatives, polyvinylalcohol, polyvinylalcohol derivatives and polyethylenglycol derivatives.

5. The solid pharmaceutical dosage form according to claim 1, which does not comprise any lubricant.

6. The solid pharmaceutical dosage form according to claim 1, which further comprises an anti-thrombotic agent, in particular acetylsalicylic acid.

7. A process for the preparation of a solid pharmaceutical dosage form according to claim 1, comprising the step of milling ticagrelor or a pharmaceutically acceptable salt or ester thereof in the presence of a polymer and/or emulsifier.

8. The process according to claim 7, wherein the milling step is carried out as wet milling or dry milling.

9. The process according to claim 7, wherein the polymer is a hydrophilic polymer.

10. The process according to claim 9, wherein the hydrophilic polymer is selected from the group consisting of cellulose derivatives, polyvinylpyrrolidone, copolymers of polyvinylpyrrolidone, polyoxyethylenealkyl ether, polyethylenglycol, co-block-polymers of ethylenoxide and propylenoxide, polymethacrylate derivatives, polyvinylalcohol, polyvinylalcohol derivatives and polyethylenglycol derivatives.

11. A solid composition comprising particles of ticagrelor or a pharmaceutically acceptable salt or ester thereof, wherein at least 90% by volume of the ticagrelor particles have a particle size in the range of 1 μm to 150 μm.

12. The solid pharmaceutical dosage form according to claim 2, wherein the weight ratio of ticagrelor or salt or ester thereof to hydrophilic polymer and/or emulsifier ranges from 100:1 to 2:1.

13. The solid pharmaceutical dosage form according to claim 4, wherein the hydrophilic polymer is a cellulose derivative selected from the group consisting of hydroxypropylmethyl cellulose, hydroxypropyl cellulose, carboxymethyl cellulose, and hydroxyethyl cellulose.

14. The solid pharmaceutical dosage form according to claim 13, wherein the cellulose derivative is in the form of a sodium or calcium salt.

15. The solid pharmaceutical dosage form according to claim 4, wherein the hydrophilic polymer is a copolymer of polyvinylpyrrolidone comprising vinylpyrrolidone and vinylacetate units.

16. The process according to claim 10, wherein the hydrophilic polymer is a cellulose derivative selected from the group consisting of hydroxypropylmethyl cellulose, hydroxypropyl cellulose, carboxymethyl cellulose, and hydroxyethyl cellulose.

17. The process according to claim 10, wherein the cellulose derivative is in the form of a sodium or calcium salt.

18. The process according to claim 10, wherein the hydrophilic polymer is a copolymer of polyvinylpyrrolidone comprising vinylpyrrolidone and vinylacetate units.

19. A solid pharmaceutical dosage form comprising more than 50% by weight of ticagrelor or salt or ester thereof in particle form, based on the total weight of the dosage form, wherein at least 90% by volume of the ticagrelor particles have a particle size in the range of 1 μm to 150 μm.

* * * * *